(12) United States Patent
Park et al.

(10) Patent No.: US 6,517,483 B2
(45) Date of Patent: Feb. 11, 2003

(54) SEALED-TYPE REMOTE PRESSURE-MONITORING DEVICE AND METHOD FOR FABRICATING THE SAME

(75) Inventors: Eun-Chul Park, Taejon-si (KR); Jun-Bo Yoon, Taejon-si (KR); Euisik Yoon, Taejon-si (KR)

(73) Assignee: Korea Advanced Institute of Science and Technology, Taejon-si (KR)

( * ) Notice: Subject to any disclaimer, the term of this patent is extended or adjusted under 35 U.S.C. 154(b) by 101 days.

(21) Appl. No.: 09/755,911

(22) Filed: Jan. 4, 2001

(65) Prior Publication Data

US 2001/0001311 A1 May 17, 2001

Related U.S. Application Data

(62) Division of application No. 09/382,353, filed on Aug. 25, 1999.

(51) Int. Cl.[7] .................................................. A61B 3/16
(52) U.S. Cl. ...................................................... 600/398
(58) Field of Search ................................. 600/373–404

(56) References Cited

U.S. PATENT DOCUMENTS

| 4,089,329 A | 5/1978 | Couvillon, Jr. |
| 4,922,913 A | 5/1990 | Waters et al. |
| 6,201,980 B1 * | 3/2001 | Darrow et al. ............... 600/347 |

OTHER PUBLICATIONS

Minature Passive Pressure Transensor for Implanting in the Eye By Carter C. Collins, IEEE Transactions on Bio–Medical Engineering vol. BME–14 No. 2 Apr. 1967, pp. 74–83.
A System for Passive Implantable Pressure Sensors By Lars Rosengren et al. Sensors and Actuators A, 43 (1994) pp. 55–58.
Wireless Micromachined Ceramic Pressure Sensors By Jennifer M. English et al. IEEE; School of Electronical and Computer Engineering, Georgia Institute of Technology, 1999.
Hermetically Sealed Inductor–Capacitor (LC) Resonator for Remote Pressure Monitoring By Eun–Chul Park, et al.Jpn.J Appl. Phys. vol. 37 (1998) pp. 7124–7128 Part 1, No. 12B Dec. 1998.

* cited by examiner

*Primary Examiner*—Max Hindenburg
*Assistant Examiner*—Pamela Wingood
(74) *Attorney, Agent, or Firm*—Bachman & LaPointe, P.C.

(57) ABSTRACT

Disclosed are a remote pressure-monitoring device and a preparing method thereof. The device comprises a metal electrode on a glass substrate, a capacitive sensor made of a silicon diaphragm, and an electroplated inductor electrically connected, in parallel, with the sensor. The glass substrate and the silicon are electrically bonded to form an LC resonator. For the fabrication of the device, first, a metal electrode which plays a role as a lower electrode for a capacitive pressure sensor is deposited on the glass substrate with the same coefficient of thermal expansion as that of silicon. An inductor is formed at a thickness by copper electroplating, surrounding the metal electrode at a predetermined distance. A silicon substrate is anisotropically etched to form a space for enveloping the metal electrode at a central area and to form a groove around the space. Boron ions are diffused lightly into the space and deeply into the groove to form etch barriers thereat, followed by bonding the silicon substrate on the glass substrate through an electrical contact in such a way that the metal electrode and the inductor are enveloped in the space and the groove, respectively. Then, the silicon substrate is etched out from its rear side to the extent that the etch barriers are exposed.

1 Claim, 8 Drawing Sheets

SEALED-TYPE REMOTE PRESSURE-MONITORING DEVICE AND METHOD FOR FABRICATING THE SAME

CROSS REFERENCE TO RELATED APPLICATION

The instant application is a divisional of U.S. patent application Ser. No. 09/382,353 filed Aug. 25, 1999 which is currently pending.

BACKGROUND OF THE INVENTION

1. Field of the Invention

The present invention relates to a sealed-type remote pressure-monitoring device. More particularly, the present invention relates to a sealed-type remote device for monitoring the internal pressures of animal organs, especially, the human eyeballs, heart, brain and so on. Also, the present invention is concerned with a method for fabricating such a device.

2. Description of the Prior Art

Medicinally, the internal pressures of human organs have significantly important meanings in treating the organs. Particularly, measuring the internal pressure of the eyeball, that is, intraocular pressure is very important because higher intraocular pressures than normal may damage visual cells. Once being damaged, the visual cells are virtually impossible to recover to a normal state. In the worst case, if not suitably treated in time, the patients may lose their sight permanently.

For this reason, extensive research has been made on methods for measuring intraocular pressures, for several decades. The intraocular pressure-sensing methods developed thus far are generally divided into a physically sensing method, an optically sensing method, and a directly sensing method using a sensor.

The physically sensing method is characterized in applying physical force to the eyeball to sense the intraocular pressure. For example, an already known pressure is applied to the eyes, followed by measuring the flexure of the eyeball. Another example of this physically sensing method is to drop glass beads or metal beads on the eyeball and then to measure the height to which they bounce.

As for the optically sensing method, it takes advantage of the change in the optical refractive index or reflection of the eyeball. For example, after a medium such as air is injected to the eyes, an optical change in the eyeball is measured. Alternatively, a reflection change-in the eyeball may be detected by applying a pressure to the eyeball.

The directly sensing method utilizes a sensor in measuring intraocular pressures. This method has an advantage over the above-mentioned indirect methods in that more accurate values for the intraocular pressure of the eyeball can be obtained by virtue of the sensor which is directly inserted in the eyes. In this regard, the pressure sensor inserted in the eyes transmits the information on the internal pressure of the eyeball to the outside by use of inductive coupling using an inductor.

Of the three representative intraocular pressure-sensing techniques, the directly sensing method has become predominant in recent years for its accuracy and convenience. In the physically or optically sensing method, a stimulus must be given to the eyeball whenever a measurement is taken on the intraocular pressure, imposing a significant burden on the patients who should be continually observed. What is worse, these indirect methods are inaccurate in sensing the internal pressures. From the late 1960s, many attempts have been made to measure intraocular pressures with the aid of wireless devices with advances in the semiconductor industry.

A remote sensing technique related to the invention is found in the article "Miniature Passive Pressure Transensor for Implantation in the Eye", IEEE Trans. BME. 14, pp. 74—83, 1967, yielded to C. C. Collins, which discloses a pressure-sensing device having two coiled inductors which are faced toward each other with a connection and sealed in a plastic package. In this structure, the plastic package is bent upon pressure application so that the distance between the two inductors varies. In turn, the mutual inductance and spray capacitance between the two coils also varies according to the change of the distance, giving rise to a change in the resonant frequency. Thus, by measuring this resonant frequency, the intraocular pressure can be monitored.

Another prior technique is exemplified by the article of L. Rogengren, entitled "A System for Passive Implantable Pressure Sensors", in Sensors and Actuators, A43, pp. 55–58, 1995. In the system, an inductor is wound around a pressure sensor made of two micromachined silicon substrates which are bonded and connected to each other in a hybrid manner. With a connection to an electrode drawn from the substrates, the inductor is enveloped in a resin. When pressure is applied to the system, the capacitance of the pressure sensor is changed, so that a corresponding change is brought about in the resonance frequency of the device because of the inductor coupled in parallel. Hence, the pressure applied can be evaluated by measuring the changed resonance frequency.

The conventional methods above mentioned, however, suffer from significant disadvantages. For instance, since the pressure-sensing device suggested in the article of C. C. Collins exposes important parts of the device externally, a plastic case harmless to the body is needed for envelopment. The system disclosed in the L. Rogengren's article is disadvantageous in that, because the pressure sensor is made of two silicon substrates, the Q value is lowered owing to the parasite capacitance between the two silicon substrates and to the hybrid coupling manner. In addition, another disadvantage of this system is that a resin is used to seal the outer inductor, requiring a harmless plastic envelope for the system.

In many patents are found the prior arts related to the present invention.

U.S. Pat. No. 4,922,913 discloses an intraocular pressure sensor which uses a piezo resistive pressure sensor. This sensor suffers from a fatal disadvantage in that, to measure the intraocular pressure of the eyeball, the sensor in the eyeball must be connected to an external.detecting device via a wire. Owing to the wire drawn from the eye, it is highly apt to be infected with bacteria and the humors in the eyeball may flow out.

Another pressure-sensing technique is disclosed in U.S. Pat. No. 4,089,329, entitled "noninvasive continuous intraocular pressure monitor". According to this invention, a change in intraocular pressure induces a motion of a strain gauge, owing to which a resistance change is caused. This resistance change is detected by a transmitter, thereby transmitting the intraocular information to the detection device without the use of wires. However, since the pressure sensor is separated from the transmitter, the humors in the eyeball may flow out.

U.S. Pat. No. 5,005,577, entitled "Intraocular lens pressure monitoring device", is similar to the C. C. Collins' article in a sensing manner, disclosing that two coiled inductors are faced toward each other with a connection and a change is brought about in the distance therebetween in dependence on pressure, allowing the spray capacitance and mutual inductance between the coils to vary. The resonance frequency thus changed is detected to monitor the changed pressure. This device, however, has a disadvantage of being enveloped in a cumbersome plastic case. The plastic case itself is not harmful to the body.

SUMMARY OF THE INVENTION

Therefore, it is an object of the present invention to overcome the above problems and to provide a sealed-type remote pressure-monitoring device, which directly allows the detection of the internal pressure of animal organs without the use of wires.

It is another object of the present invention to provide a sealed-type remote pressure-monitoring device, which itself can be inserted into the body without being packed in harmless plastic.

It is a further object of the present invention to provide a sealed-type remote pressure-monitoring device, by which the internal pressure of animal organs can be measured with high accuracy.

It is still a further object of the present invention to provide a sealed-type remote pressure-monitoring device, which has few parasitic components in the pressure sensor and a reduced resistance in an inductor so as to obtain a high Q value.

It is still another object of the present invention to provide a method for fabricating such a sealed-type remote pressure-monitoring device.

Viewed from a first aspect, the present invention provides a device for remote monitoring the internal pressure of animal organs, said device comprising: a glass substrate having a coefficient of thermal expansion as large as that of silicon; a metal electrode which is formed at a predetermined thickness on a central area of the glass substrate; an inductor which is formed at a predetermined thickness on the glass substrate by a copper electroplating process, surrounding the metal electrode at a predetermined distance; a silicon cover, consisting of a silicon diaphragm and a cover structure, which is bonded on the glass substrate in such a manner that the silicon diaphragm and the cover structure cover the metal electrode and the inductor, respectively, without a direct contact between them, thereby shielding the metal electrode and the inductor from the external environment; a contact which is formed on the glass substrate, extending from a junction between the glass substrate and the silicon cover to the inductor to electrically connect the silicon cover to the inductor.

Viewed from a second aspect, the present invention provides a method for fabricating a sealed-type device which remotely senses the internal pressure of animal organs, said method comprising the step of: depositing a metal electrode on a central area of a glass substrate with a coefficient of thermal expansion as large as that of silicon, the metal electrode playing a role as a lower electrode for a capacitive pressure sensor; forming a pattern of an inductor at a predetermined thickness by copper electroplating, said inductor surrounding the metal electrode at a predetermined distance; etching a central area of a silicon substrate to form a space for enveloping the metal electrode; forming a pattern of a groove around the space in the silicon substrate by a etching process; diffusing boron ions shallowly into the space and deeply into the groove to form etch barriers thereat; bonding the silicon substrate on the glass substrate through an electrical contact in such a way that the metal electrode and the inductor are enveloped in the space and the groove, respectively; and etching the silicon substrate from its rear side to the extent that the etch barriers are exposed.

BRIEF DESCRIPTION OF THE DRAWINGS

The above and other objectives and aspects of the invention will become apparent from the following description of embodiments with reference to the accompanying drawings in which.

DETAILED DESCRIPTION OF THE PREFERRED EMBODIMENTS

Figure 1:
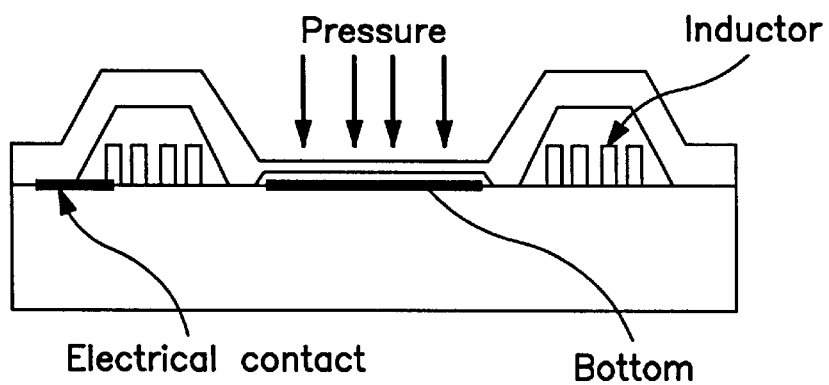
FIG. 1 is a cross sectional view of a remote pressure-monitoring device according to the present invention.

The application of the preferred embodiments of the present invention is best understood with reference to the accompanying drawings, wherein like reference numerals are used for like and corresponding parts, respectively.

In the present invention, a glass substrate and a silicon substrate, both harmless to the human body, are used as base materials in fabricating an intraocular pressure sensor, so that no additional packages are needed for the sake of securing safety. While the glass substrate is provided to integrate a sensor and a transmitter thereon according to a semiconductor process, it is electrically combined with the silicon substrate in such a manner that the sensor and transmitter are sealed. In detail, when the silicon substrate and the glass substrate are put together, the resulting united module comes to have a structure in which the pressure sensor and an inductor are concealed. Therefore, not only the capacitive pressure sensor, but also the inductor is sealed per se, so no packages are needed.

Since Au deposited on the glass substrate and boron-diffused silicon diaphragm are used as a lower electrode and an upper electrode of the capacitive pressure sensor, the device of the present invention has far fewer parasitic components than have the conventional pressure sensors which are made of two laminated silicons. Also, the present invention is characterized in that all of the parts of the device, except for the silicon diaphragm and the glass substrate, both harmless to the human body, are per se sealed by integrating the inductor and the capacitance in the chip. Therefore, the device itself can be inserted into the body without being packed in, for example, harmless plastic.

With reference to FIGS. 1 to 5, there is illustrated an LC-resonant pressure-monitoring device according to the present invention.

Figure 2:
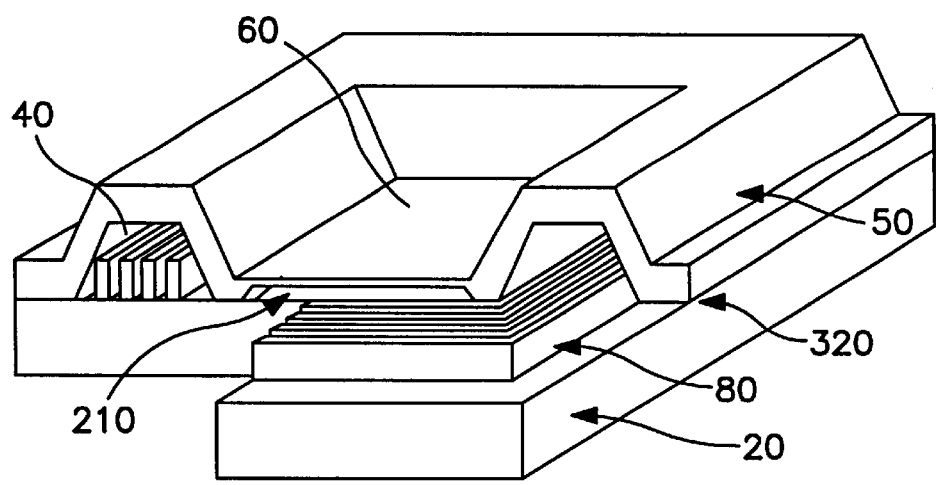
FIG. 2 is a partially broken perspective view of the remote pressure-monitoring device shown in FIG. 1.
Figure 3:
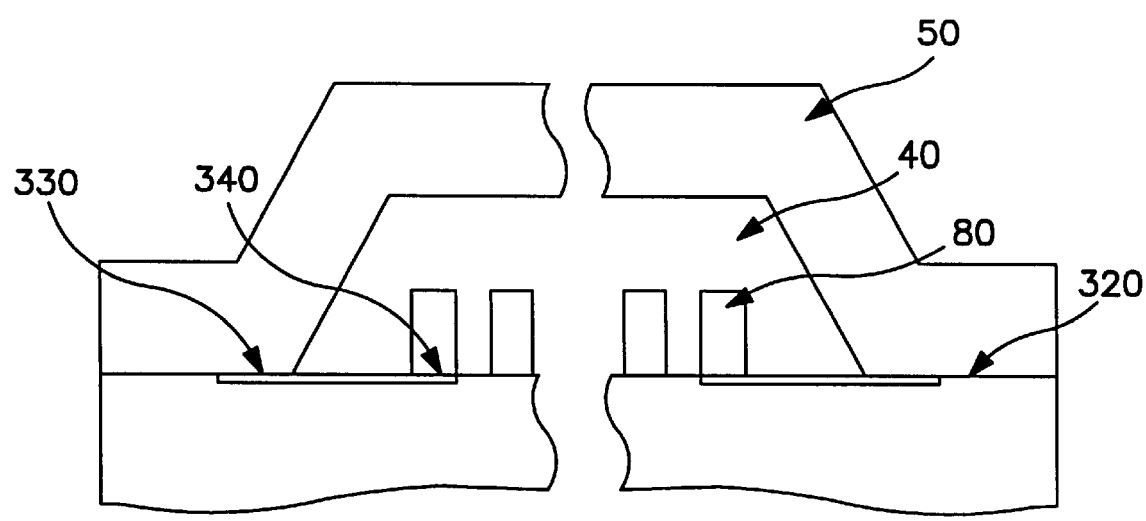
FIG. 3 is an illustration for explaining an electrical contact between an inductor and a capacitive pressure sensor in the remote pressure-monitoring device according to the present invention.
Figure 4:
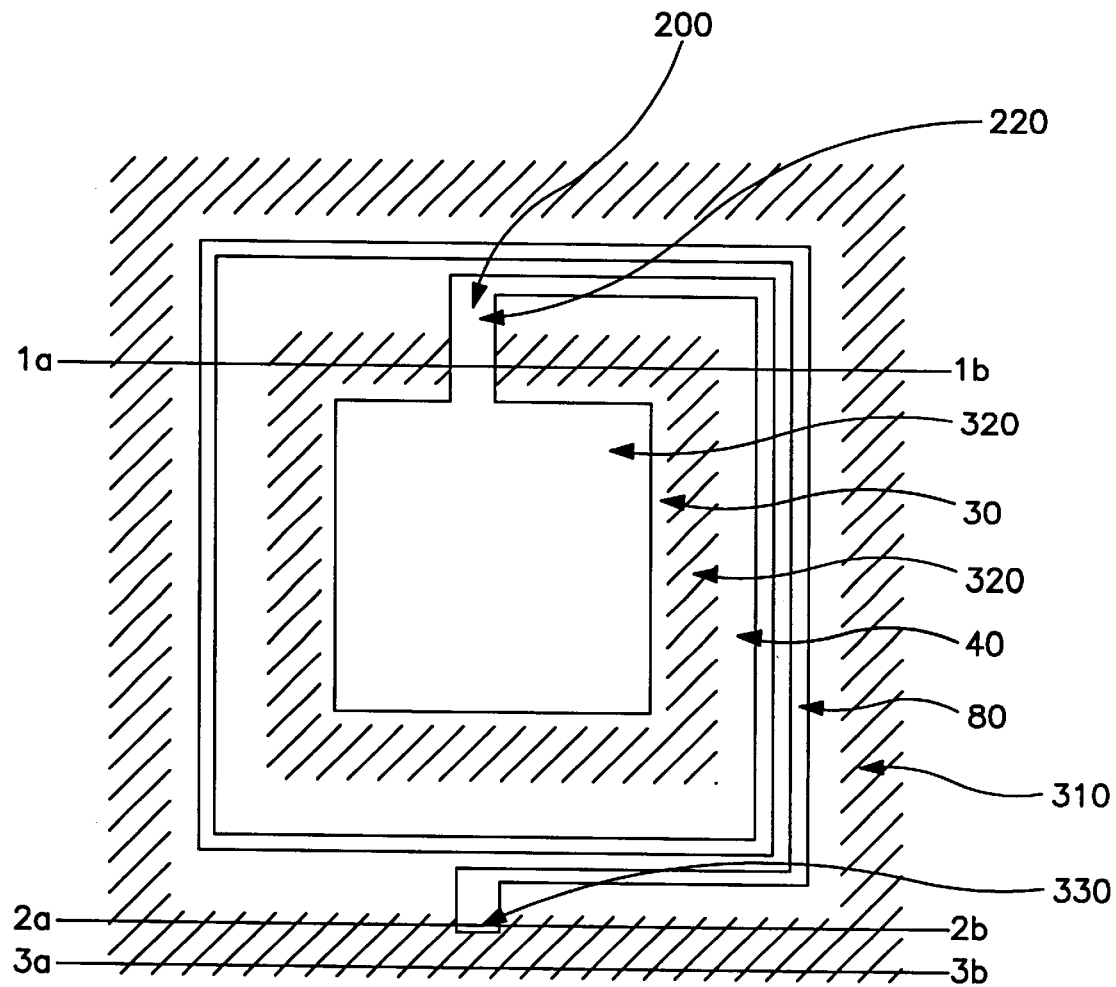
FIG. 4 is a schematic plan view of the remote pressure-monitoring device viewed from the view point of a glass substrate.
Figure 5A:
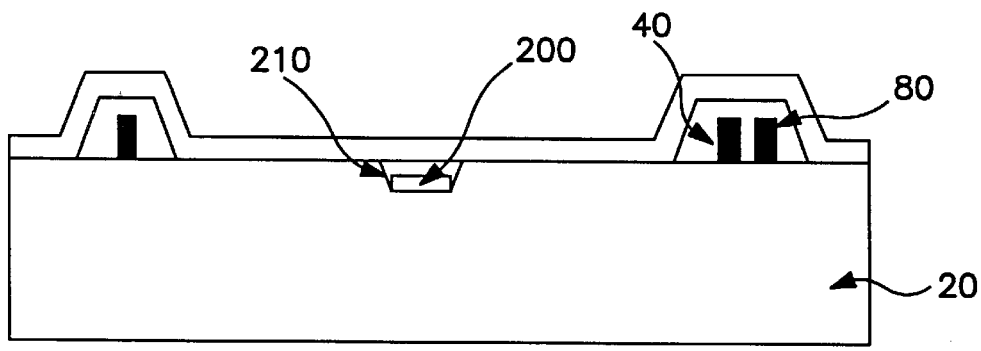
FIGS. 5a to 5c are cross sectional views taken along lines shown in FIG. 4.
Figure 5B:
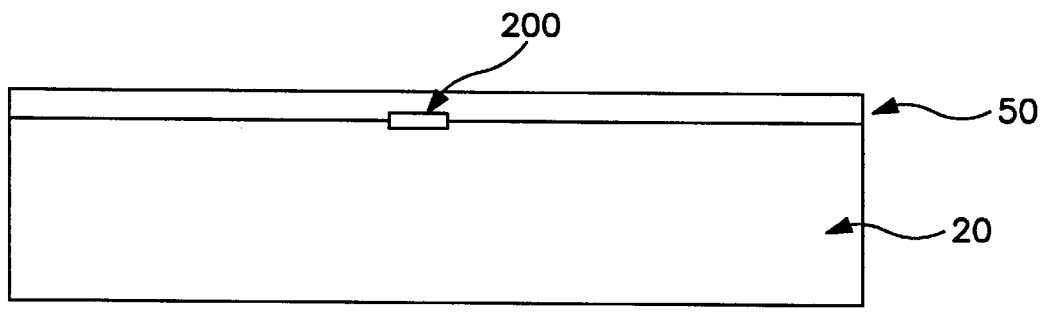
Figure 5C:
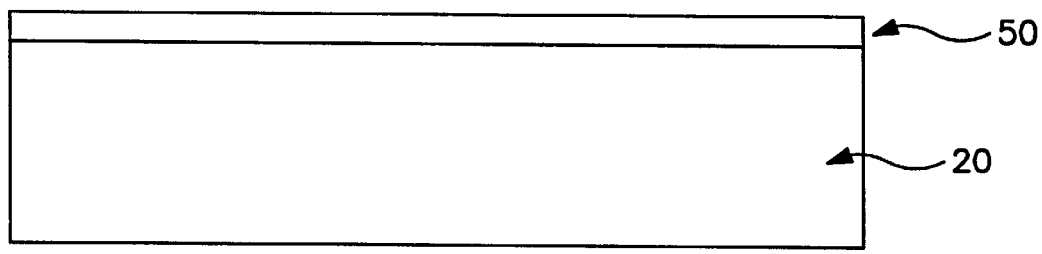

FIG. 1 shows the structure of the LC-resonant pressure monitoring device in a cross sectional view while FIG. 2 is a partially broken perspective view of the device. As shown in these figures, the device comprises a glass substrate 20 with a metal electrode 210 formed at a predetermined thickness on a central area of the glass substrate, an inductor 80 formed at a predetermined thickness on the glass substrate 20, surrounding the metal electrode 210 at a predetermined distance, and a silicon cover 50 consisting of a silicon diaphragm 60 and a cover structure 40, bonded on the glass substrate 20, said diaphragm 60 covering the metal electrode 210, said cover structure 40 accommodating the inductor 80. Thus, the silicon cover plays a role in shielding the metal electrode and the inductor from the external environment. On the glass substrate 20 is formed a contact through which the silicon cover 50 is electrically connected to the inductor 80. The glass substrate 20 is made of Corning 7740 with a coefficient of thermal expansion as large as that of the silicon substrate 10, so the thermal stress generated owing to the difference in the coefficient of thermal expansion when bonding the silicon substrate 10 on the glass substrate 20 can be minimized.

A method for fabricating the device is described in FIGS. 5a to 5c and FIG. 6.

The fabrication of the remote intraocular pressure-measuring device is conducted in two processes: a silicon substrate process and a glass substrate process. The silicon substrate and the glass substrate which are obtained by conducting the two processes, respectively, are combined by anode bonding.

First, the glass substrate process is sub-divided into a metal depositing step and a copper plating step by which the lower electrode 210 of the capacitive pressure sensor and the inductor 80 are formed, respectively. The planar glass substrate 20 is etched to a depth of 200 nm at its central region, followed by depositing Au/Cr in a thickness of 220 to 230 nm on the etched central region to form a metal electrode 70. As a result, this metal electrode 70 becomes higher than the glass substrate 20 by approximately 20 to 30 nm. The reason why the metal electrode 70 is made at such a height is that, when the silicon substrate 10 obtained by the silicon process is electrically bonded on the glass substrate 20, the silicon substrate 10 and the inductor 80 are each optimally brought into an electrical contact, as denoted the reference numerals 330 and 340 in FIG. 3, with an electrical junction between the capacitive sensor and the inductor 80.

For the formation of the inductor 80, copper electroplating is useful. Preferably, the copper used in the present invention has an electric conductivity ($\rho$) as high as about 1.7 $\mu\Omega$. In order for the inductor 80 to have a high Q value, it must be of small resistance and large inductance. Plating the copper at a large thickness can reduce the resistance while narrowing the space between inductor lines can increase the inductance. Accordingly, a photoresist film 100 is patterned at a high aspect ratio. In the present invention, copper is electroplated at a thickness of 30 $\mu$m and used to obtain a photoresist 100 in which the ratio of line to space is 15 $\mu$m/15 $\mu$m.

The process which is performed on the silicon substrate comprises etching and diffusing.

Figure 6:
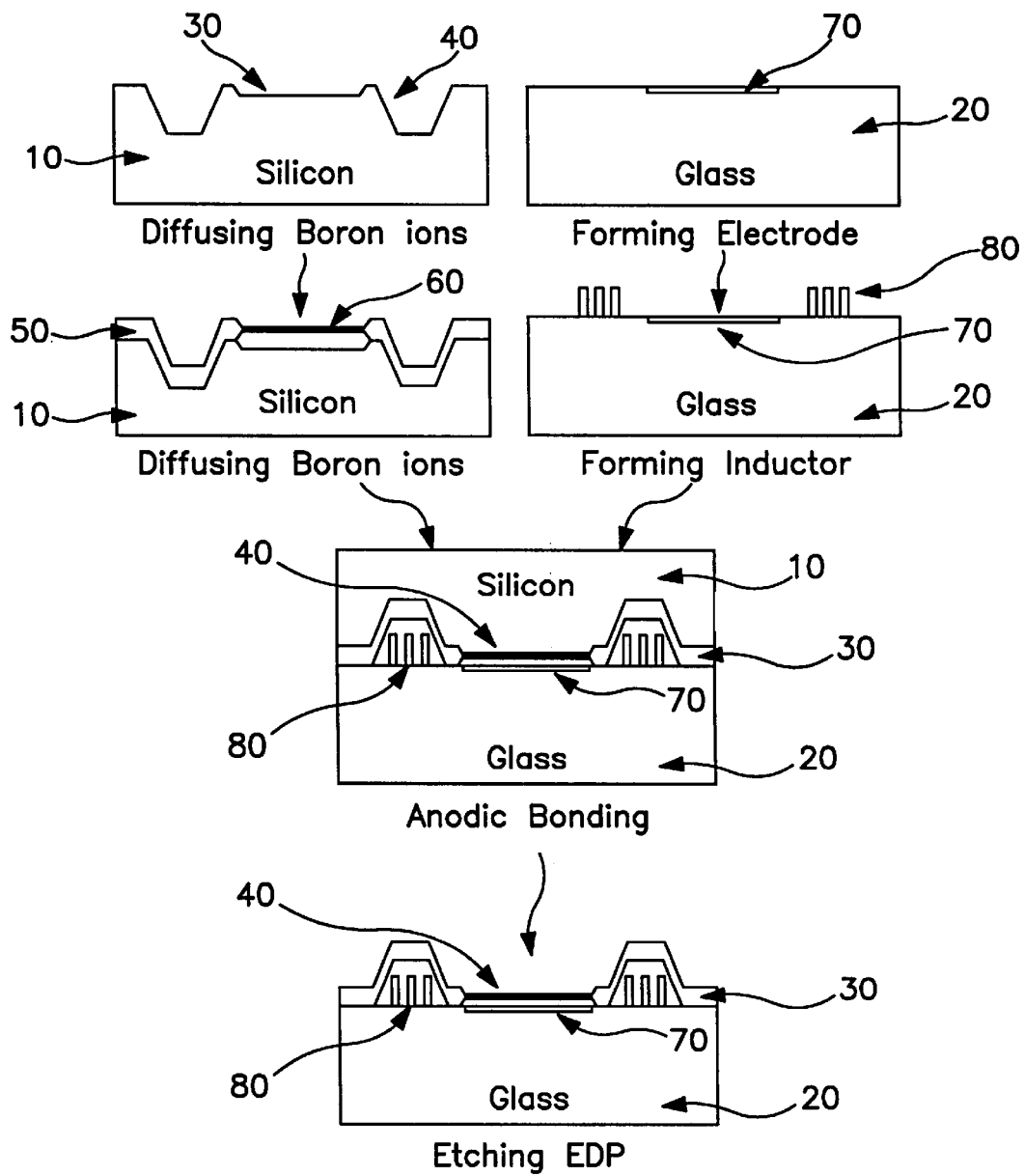
FIG. 6 is an illustration for explaining the process for fabricating the remote pressure-monitoring device according to the present invention.

First, as for the etching, it is conducted to form a space 30 for separating the silicon substrate 10 from the metal electrode 70 formed on the glass substrate 20 and to form a groove 40 for accommodating and protecting the inductor 80. To this end, the silicon substrate 10 is anisotropically etched using KOH. Following this, boron is diffused on the etched areas, that is, the space 30 for the capacitive sensor and the groove 40 for the inductor, to form etch-preventive films 50 and 60, as illustrated in FIG. 6.

Next, the resulting silicon substrate 10 is aligned with the glass substrate 20 in such a way that the space 30 and the groove 40 correspond to the metal electrode 70 and the inductor 80, respectively. Subsequently, the silicon substrate 10 and the glass substrate 20 are subjected to an electrical bonding process at 400° C. and 800 V.

Thus, the inductor 80 is electrically connected to the capacitance and finally, the silicon 10 is electrically bonded on the glass substrate 20. Thereafter, the silicon substrate 10 is etched out from its rear until the etch-preventive film remains alone.

Figure 7:
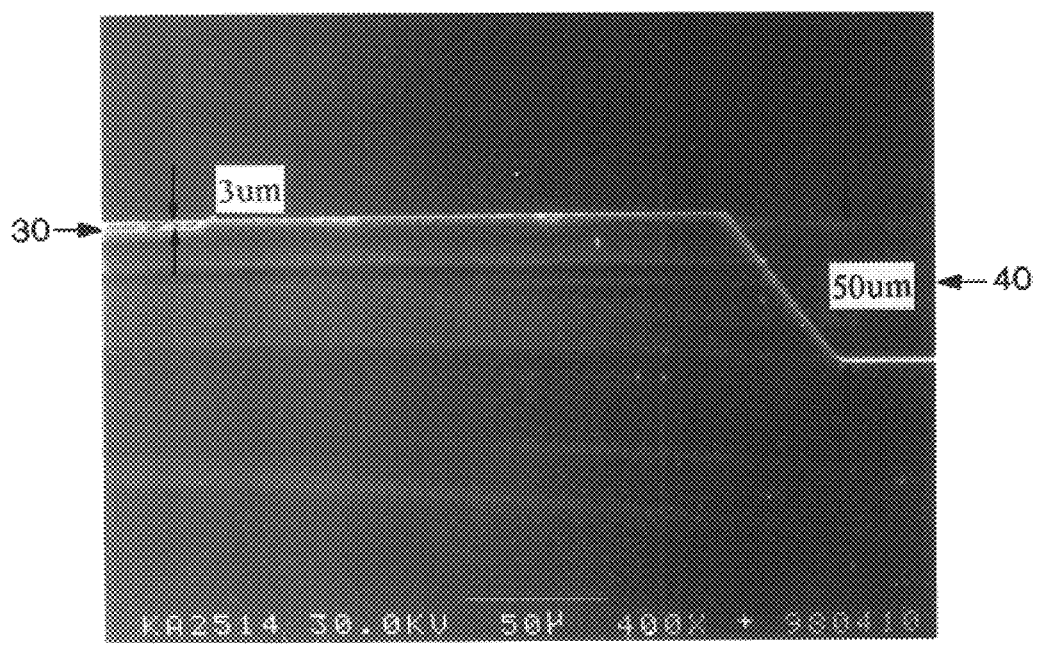
FIG. 7 is an electron micrography showing a portion of the remote pressure-monitoring device, in which the silicon substrate is etched at thicknesses of 3 $\mu$m and 50 $\mu$m to form a space for a capacitor electrode and a groove for the inductor.
Figure 8:
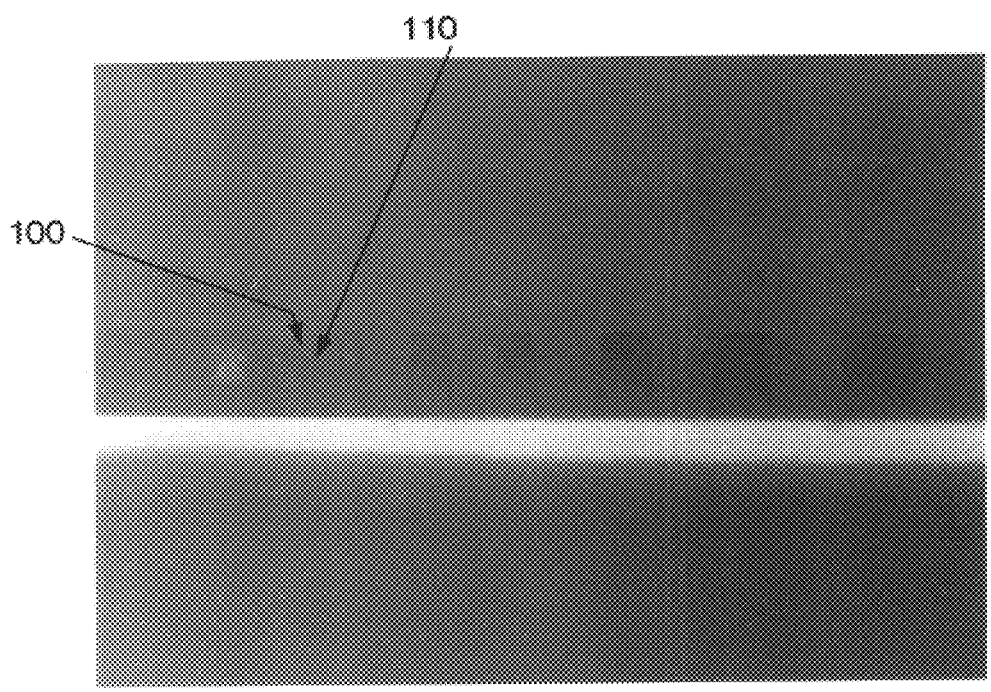
FIG. 8 is an optical micrograph showing a pattern of a photoresist film 30 $\mu$m thick.
Figure 9:
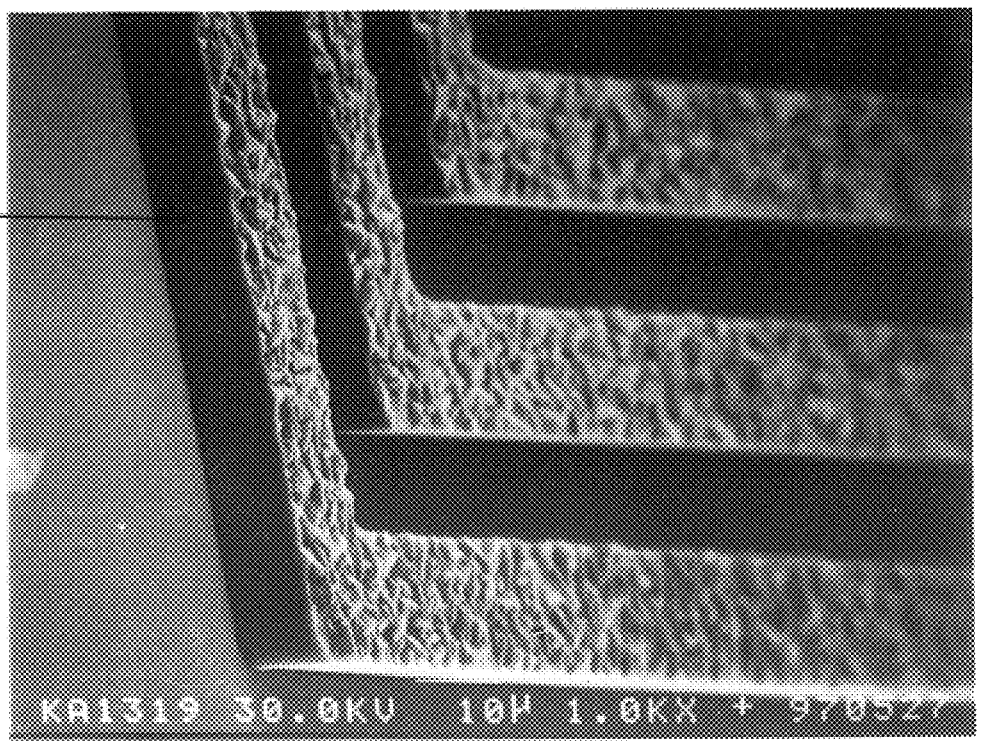
FIG. 9 is an electron micrograph showing inductor coils 30 $\mu$m thick formed by copper electroplating.

During the fabrication of the sealed-type remote pressure-monitoring device according to the above procedure, important parts had their microphotographs taken, as shown in is FIGS. 7 to 9.

In the electron micrograph of FIG. 7, there are shown the space 30 for the capacitor electrode and the groove 40 for the inductor, which are etched to a depth of 3 $\mu$m and 50 $\mu$m, respectively. FIG. 8 shows a pattern of the photoresist film 100 which is 30 $\mu$m thick, in an optical micrograph. The inductor coils 80 which are formed at a thickness of 30 $\mu$m by a copper electroplating process are shown in the electron micrograph of FIG. 9.

The pressure-monitoring device of the present invention, as illustrated above, has a structure in which the inductor is in parallel connected to a variable capacitive pressure sensor. Varying with pressure, the capacitive pressure sensor consists of a $P^+$-diffused silicon film 60 and the metal electrode 210 deposited on the glass substrate 20. When being applied with pressure, the silicon diaphragm is warped to alter the capacitance of the capacitive pressure sensor. The pressure-monitoring device according to the present invention is designed to have its resonant frequency vary in dependence on the capacitance. Therefore, a change in the resonant frequency indicates a change in the pressure, enabling evaluation of the internal pressure.

Figure 10:
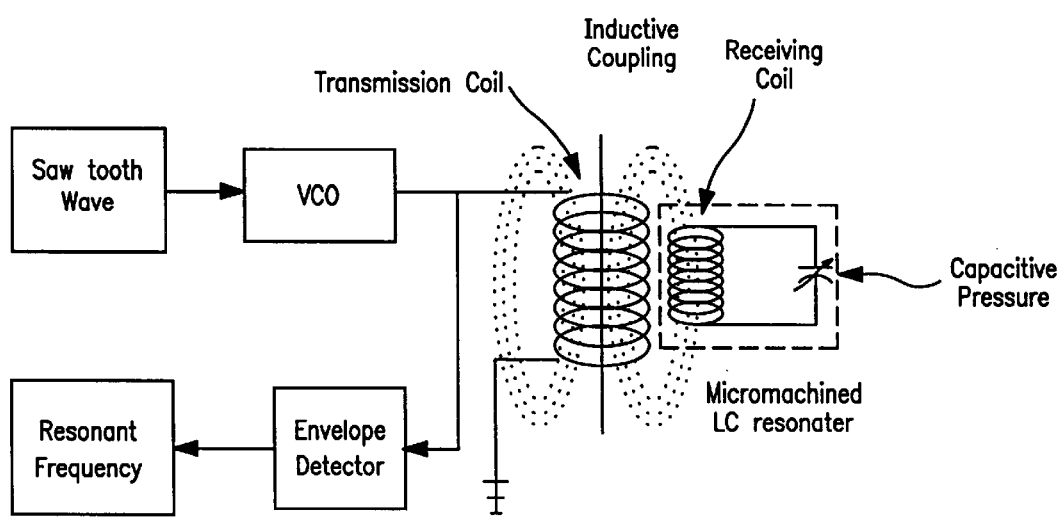
FIG. 10 is a schematic diagram illustrating a remote pressure-monitoring procedure.

With reference to FIG. 10, the principle under which the pressure-monitoring device of the present invention is operated is illustrated. If an external saw tooth wave drives a VCO, the voltage across the opposite ends of a driving coil suddenly changes when being measured around the resonance frequency of the pressure-monitoring device. This change of the voltage is attributed to the fact that the LC resonance causes the output impedance from the driving coil to suddenly vary around the resonance frequency of the pressure device. At this time, this variation allows the resonance frequency of the pressure-monitoring device to be calculated, thereby measuring the pressure applied to the pressure-monitoring device.

As described hereinbefore, the remote pressure-monitoring device of the present invent on can measure intraocular pressure with high accuracy without the aid of a wire and has a structure in which the sensor and its important parts are sealed per se. Therefore, in addition to being accurate and safe, therefore, the device itself needs no packages.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A device for remote monitoring the internal pressure of animal organs, said device comprising:

a glass substrate having a coefficient of thermal expansion as large as that of silicon;

a metal electrode which is formed at a predetermined thickness on a central area of the glass substrate;

an inductor which is formed at a predetermined thickness on the glass substrate by a copper electroplating process, surrounding the metal electrode at a predetermined distance;

a silicon cover, consisting of a silicon diaphragm and a cover structure, which is bonded on the glass substrate in such a manner that the silicon diaphragm and the cover structure cover the metal electrode and the inductor, respectively, without a direct contact between them, thereby shielding the metal electrode and the inductor from the external environment;

a contact which is formed on the glass substrate, extending from a junction between the glass substrate and the silicon cover to the inductor to electrically connect the silicon cover to the inductor.

* * * * *